United States Patent
Nandy et al.

(10) Patent No.: US 11,401,499 B2
(45) Date of Patent: Aug. 2, 2022

(54) FERMENTATION MEDIUM FOR GROWTH OF METHANOTROPHIC BACTERIA AND METHOD FOR PRODUCING SAID MEDIUM

(71) Applicant: UNIBIO A/S, Odense (DK)

(72) Inventors: Subir Kumar Nandy, Kongens Lyngby (DK); Ib Christensen, Allerod (DK); Budi Juliman Hidayat, Hvidovre (DK)

(73) Assignee: UNIBIO A/S, Odense M (DK)

( * ) Notice: Subject to any disclaimer, the term of this patent is extended or adjusted under 35 U.S.C. 154(b) by 159 days.

(21) Appl. No.: 16/490,156

(22) PCT Filed: Feb. 28, 2018

(86) PCT No.: PCT/EP2018/054947
§ 371 (c)(1),
(2) Date: Aug. 30, 2019

(87) PCT Pub. No.: WO2018/158322
PCT Pub. Date: Sep. 7, 2018

(65) Prior Publication Data
US 2020/0063090 A1 Feb. 27, 2020

(30) Foreign Application Priority Data
Mar. 1, 2017 (DK) .......................... PA 2017 00143

(51) Int. Cl.
*C12N 1/20* (2006.01)
*A23K 10/12* (2016.01)

(52) U.S. Cl.
CPC .............. *C12N 1/20* (2013.01); *A23K 10/12* (2016.05); *C12N 2500/20* (2013.01); *C12N 2500/22* (2013.01); *C12N 2500/24* (2013.01)

(58) Field of Classification Search
CPC ....... Y02E 50/30; Y02E 50/10; Y02E 50/343; Y02E 50/17; Y02E 50/16; C12P 7/04; C12P 7/08; C12P 5/002; C12P 5/007; C12P 5/026; C12P 7/02; C12P 7/42; C12P 5/023; C12P 7/065; C12P 7/54; C12P 2201/00; C12P 7/10; C12P 7/56; C12P 1/04; C12P 7/00; C12P 7/16; C12P 7/22; C12P 7/52; C12P 7/6427; C12P 7/6472; C12R 1/145; C12R 1/07; C12N 9/88; C12N 15/70; C12N 9/0006; C12N 9/0008; C12N 9/1025; C12N 9/1029; C12N 9/1217; C12N 9/18; C12N 11/04; C12N 11/08; C12N 1/20; C12N 11/089; C12N 15/00; C12N 1/32; C12N 2500/24; C12Y 101/01027; C12Y 101/01034; C12Y 101/01037; C12Y 102/01051; C12Y 102/04001; C12Y 203/01008; C12Y 203/01016; C12Y 203/03001; C12Y 203/0301; C12Y 207/02001; C12Y 301/01031; C12Y 401/01031; B33Y 80/00; B33Y 10/00; C12M 21/04; C12M 23/24; C12M 29/04; C12M 29/18; C12M 43/02; C12M 21/00; C12M 21/18; C12M 1/06; C12M 21/02; C12M 21/12; C12M 25/14; C12M 25/16; C12M 41/40; C02F 11/08; C02F 3/286; C02F 3/34; C02F 9/00; Y02W 10/10; Y02W 10/12; A23K 10/12; B01J 31/003; B01J 31/06; C12Q 1/68; Y02P 20/54
See application file for complete search history.

(56) References Cited

U.S. PATENT DOCUMENTS

| | | | |
|---|---|---|---|
| 3,996,105 A | 12/1976 | Harrison et al. | |
| 2006/0045871 A1* | 3/2006 | Odom | A23K 50/80 424/93.4 |
| 2013/0324407 A1 | 12/2013 | Bogosian | |
| 2015/0111265 A1 | 4/2015 | Lidstrom et al. | |

FOREIGN PATENT DOCUMENTS

| | | |
|---|---|---|
| GB | 1522479 A | 8/1978 |
| SU | 908085 A1 | 12/1979 |
| SU | 770200 A | 3/1987 |
| WO | 03/016460 A1 | 2/2003 |

OTHER PUBLICATIONS

Machine translation of SU770200A1 from Russian into English, 2 pages.
Machine translation of SU908085 from Russian into English, 4 pages.
Translation from Russian to English of Search Report from Federal Institute of Industrial Property (FIPS), completed Jul. 14, 2021, 2 pages.
Search Report from Federal Institute of Industrial Property (FIPS) in Russian language, completed Jul. 2021, 2 pages.
Scandanavian Culture Collection for Algae & Protozoa: L1 & L1-M (L1-Si, L1-Si+NH4); www.sccap.dk [online] [retrieved on Aug. 24, 2017 using www.archive.org dated Dec. 8, 2015]; retrieved from the Internet URL: https//web.archive.org/web/20151208145137/http://www.sccap.dk/media/marine/2.asp>See "3.Trace metal working stock solution", 2 pages.

(Continued)

*Primary Examiner* — Michelle F. Paguio Frising
(74) *Attorney, Agent, or Firm* — Ware, Fressola, Maguire & Barber LLP

(57) ABSTRACT

The present invention relates to a method for providing a fermentation medium for the cultivation of at least one methanotrophic organism, or for the cultivation of a combination of organisms comprising at least one methanotrophic organism, the method comprises the step of: (i) providing a main growth solution; (ii) optionally sterilizing the main growth solution provided in step (i); (iii) providing a trace metal solution; and (iv) mixing the main growth solution (as provided in step (i) or (ii)) with the trace metal solution provided in step (iii) and providing the fermentation medium for the cultivation of at least one methanotrophic organism, or for the cultivation of a combination of organisms comprising at least one methanotrophic organism.

20 Claims, No Drawings

(56) References Cited

OTHER PUBLICATIONS

Hill, T.W., and E. Kafer (2001), "Improved protocols for Aspergillus minimal medium: trace element and minimal medium salt stock solutions," Fungal Genetics Reports: vol. 48, Article 8. https://doi.org/10.4148/1941-4765.1173, 4 pages.

Microorganisms, DSMZ, 732. Dehalobacter Restricttus Medium (TCE); www.dsmz.de [online]; [retrieved on Sep. 5, 2017 using www.archive.org dated May 3, 2015]; Retrieved from the Internet <URL: https://web.archive.org/web/20150503115054/http://www.dsmz.de/microorganisms/medium/pdf/DSMZ_Medium_Medium732.pdf>, 2007 DSMZ GmbH, 2 pages.

Danish Patent and Trademark Office, Search Report, Patent Application No. PA 2017 00143, completed Sep. 5, 2017, 4 pages.

International Search Report (ISR), International application No. PCT/EP2018/054947, ISR dated May 2, 2018, 2 pages.

Methanotrophs Commons: "General Culturing Tips," Oct. 31, 2013, XP002780008, Retrieved from the Internet: URL:http://www.methanotroph.org/wiki/culturings-tips/ [retrieved on Apr. 12, 2018], 11 pages.

Bothe H et al: "Heterotrophic bacteria growing in association with *Methylococcus capsulatus* (Bath) in a single cell protein production process," Applied Microbiology and Biotechnology, Springer, DE, vol. 59, No. 1, Jun. 1, 2002, 7 pages.

Larsen J et al: "Reduction of RNA and DNA inby endogenous nucleases," Applied Microbiology and Biotechnology, Springer, DE, vol. 45, No. 1-2, Mar. 1, 1996, 7 pages.

\* cited by examiner

FERMENTATION MEDIUM FOR GROWTH OF METHANOTROPHIC BACTERIA AND METHOD FOR PRODUCING SAID MEDIUM

TECHNICAL FIELD OF THE INVENTION

The present invention relates to an improved fermentation medium for the cultivation of methanotrophic organisms. In particular, the present invention relates to process for providing an improved fermentation medium.

BACKGROUND OF THE INVENTION

One of the main food resources for humans may come from meat from animals and fish, beans and peas, eggs, processed soy products, nuts, seeds etc. because of the high content of protein in the products, which has an important nutritional benefit effect on the human body and development.

Not only humans have an increasing demand for a protein rich diet, but also animals (pets or farmed animals) and fish are feed more protein rich diet in order to speed up growth and development and for the wellbeing of the animal.

However, with an increasing world population, reaching 9 billion by 2050, and an increasing demand for proteins in the animal farming and pet industry, there is strong evidence that agriculture will not be able to meet this demand and that there is serious risk of food shortage.

To meet this demand production of single cell protein (SCP) has shown to be a very interesting candidate as these SCP may be grown by fermentation of biomass through the growth of the microorganisms on hydrocarbon, nitrogen and other substrates. SCP production represents options of failsafe mass food-production which can produce food reliably worldwide and even under harsh climate conditions.

SCP product may be used directly in food or feed products, e.g. as a liquid product or as a spray dried product. The SCP or the biomass may alternatively be further processed, e.g. by hydrolysis and/or separation, to provide special fractions, remove impurities or concentrating components, before use in a food or feed product.

For commercial production of e.g. SCP the fermentation process involves 3 fermentation stages:

A batch fermentation; which is the initial propagation of the organisms where all materials except the organisms, required are decontaminated by autoclaving before, loaded to the reactor together with the organisms and the process starts. The organism used goes through all the growth phases (lag phase, exponential phase and steady state phase. Under this operation mode, conditions are continuously changed with time under unsteady-state system and require a lot work and involvement.

A fed-batch fermentation; is a biotechnological operational process where one or more nutrients are feed to the bioreactor during cultivation and in which the product/s remain in the bioreactor until the end of the run. The fed-batch fermentation is following the batch fermentation and is provided to achieve very high cell concentrations of the organism, as batch fermentation would require inhibitory high concentrations of nutrients and would therefore not be possible. The fed-batch fermentation is preparing the cell culture for continuous fermentation.

A continuous fermentation; is the production mode of the fermentation process where feeding the microorganism with sterile fermentation medium which is used for the cultivation of the organism and at the same time, removing part of the fermentation liquid comprising the cells with spent medium from the system. This makes a unique feature of continuous culture which is that a time-dependent steady-state that can be attained and which enables one to determine the relations between environmental conditions and microbial behaviour including both genetic and phenotypic expression.

For financial reasons, there is an interest and a drive in the industry to start the continuous and steady state fermentation as quickly as possible to save time and costs and provide the SCP product faster and profitable to the market.

Therefore, the traditional provided processes use a nitrate compound as the nitrogen source during the batch fermentation, which is a small-scale fermentation. When changing to fed-batch, which is a large-scale fermentation, where the biomass content is to be increased and the demand for nitrogen is significantly increased compared to the batch phase. Thus, in order to speed up the growth of the organism and to save costs on the nutrients, the nitrogen source is changed to an ammonium compound. During the continuous fermentation, the steady state fermentation, which is the large-scale production of the SCP where a constant of fermentation liquid comprising the biomass is withdrawn from the fermentation reactor together with addition of a constant volume fermentation medium. During this continuous fermentation, the steady state fermentation, the nitrogen source is changed to an ammonium compound.

The challenge of using ammonium as the nitrogen source is that there is a significant increased risk of poisoning the fermentation liquid with nitrite which may be formed when ammonia is oxidized under nitrification process which is the rate limiting step of nitrification. During nitrification, the microorganism is under extreme stress and nitrite may be formed. Since nitrite cannot be converted totally into nitrate the fermentation must be stopped and discarded and a new batch must be started. This process is called the route of death of the fermentation and is feared by all single cell protein produces.

Hence, an improved fermentation medium would be advantageous, and in particular it would be advantageous to provide a fermentation medium being more efficient, more reliable, capable of providing a faster growth, reducing the risk of failure, and without compromising the cost challenge in the industry.

SUMMARY OF THE INVENTION

Thus, an object of the present invention relates to an improved fermentation medium.

In particular, it is an object of the present invention to provide a new method of providing an improved fermentation medium that solves the above-mentioned problems of the prior art with cost, effectivity, speed of the fermentation, risk of failure and cost.

Thus, one aspect of the invention relates to a method for providing a fermentation medium for the cultivation of at least one methanotrophic organism, or for the cultivation of a combination of organisms comprising at least one methanotrophic organism, the method comprises the step of:

(i) providing a main growth solution;
(ii) optionally sterilizing the main growth solution provided in step (i);
(iii) providing a trace metal solution;
(iv) mixing the main growth solution (as provided in step (i) or (ii)) with the trace metal solution provided in step (iii) and providing the fermentation medium for the cultivation of at least one methanotrophic organism, or for the cultivation of a combination of organisms comprising at least one methanotrophic organism, wherein the trace metal solution is provided in a two-step procedure and wherein the two-step procedure involves:
- (v) providing at least one precipitating trace metal compound;
- (vi) providing one or more trace metals,
- (vii) mixing the at least one precipitating trace metal compound (provided in step (v)) and the one or more trace metal (provided in step (vi)), providing the trace metal solution;

wherein an acid is added to the precipitating trace metal compound, or to the one or more trace metal or to both the precipitating trace metal compound and to the one or more trace metal, providing an acidic dissolved composition, before the at least one precipitating trace metal compound (provided in step (v)) and the one or more trace metal (provided in step (vi)) are mixed, providing the trace metal solution.

Another aspect of the present invention relates to a fermentation medium obtainable by the method according to the present invention.

A further aspect of the present invention relates to a fermentation medium comprising the following constituents: water; one or more calcium compounds, in particular calcium chloride; an acidic dissolved precipitating trace metal compound; one or more trace metals; and one or more buffer solutions, wherein none of the constituent's precipitates.

Yet another aspect of the present invention relates to a fermentation reactor comprising a reactor tank, one or more fermentation medium inlet, a fermentation liquid outlet for withdrawing fermentation liquid from the fermentation reactor and an ion sensor or analyser.

Still another aspect of the present invention relates to a fermentation process for production of biomass by cultivating at least one methanotrophic organism, or a combination of organisms comprising at least one methanotrophic organism, the method comprises the step of:
- (a) adding at least one methanotrophic organism into a fermentation reactor;
- (b) supplying a fermentation medium according to the present invention to the fermentation reactor,
- (c) Allowing the at least one methanotrophic organism present in the fermentation medium to ferment, providing a fermentation liquid; and
- (d) recovering the fermentation liquid from the fermentation reactor providing the biomass.

An even further aspect of the present invention relates to a biomass product obtainable by the fermentation process according to the present invention.

A further aspect of the present invention relates to a protein product obtainable by the fermentation process according to the present invention.

A further aspect of the present invention relates to a food or feed product comprising the biomass product according to the present invention; or the protein product according to the present invention.

Yet an aspect of the present invention relates to the use of the feed product according to the present invention for preparing a fish feed or an animal feed, such as a pig feed, a cow feed, or a chicken feed.

DETAILED DESCRIPTION OF THE INVENTION

Methanotrophic organism, such a bacteria of the family Methylococcaceae (which are known as consuming methane as main carbon source) have previously been propagated during batch fermentation and fed batch fermentation in different media, such as Nitrate mineral salts medium (NMS) or Ammonium mineral salts (AMS) with a low growth rate resulting in a batch fermentation process of about 120 hours and resulting in a fed-batch fermentation process of about 480 hours. As mentioned above when discussing the prior art, there is still a need for providing improved media for propagating methane utilizing methanotrophic organisms, such as bacteria of the family Methylococcaceae, which media can result in a faster growth rate, higher yield of cells, and of cells having an improved viability, reducing the chance of precipitation of substrate composition, minimizing the risk for contamination during the process and moreover has some advantages over preventing the inhibition if any toxic product formed, and reduce the time to start before continuous fermentation (production fermentation), thereby reducing the cost of production.

Accordingly, a preferred embodiment of the present invention relates to a method for providing a fermentation medium for the cultivation of at least one methanotrophic organism, or for the cultivation of a combination of organisms comprising at least one methanotrophic organism, the method comprises the step of:
- (i) providing a main growth solution;
- (ii) optionally sterilizing the main growth solution provided in step (i);
- (iii) providing a trace metal solution;
- (iv) mixing the main growth solution (as provided in step (i) or (ii)) with the trace metal solution provided in step (iii) and providing the fermentation medium for the cultivation of at least one methanotrophic organism, or for the cultivation of a combination of organisms comprising at least one methanotrophic organism.

wherein the trace metal solution is provided in a two-step procedure and wherein the two-step procedure involves:
- (v) providing at least one precipitating trace metal compound;
- (vi) providing one or more trace metals;
- (vii) mixing the at least one precipitating trace metal compound (provided in step (v)) and the one or more trace metal (provided in step (vi)), providing the trace metal solution;

wherein the at least one precipitating trace metal compound; the one or more trace metal; or to both the precipitating trace metal compound and to the one or more trace metal may be dissolved before the at least one precipitating trace metal compound (provided in step (v)) and the one or more trace metal (provided in step (vi)) are mixed, providing the trace metal solution.

In the context of the present invention, the term "main growth solution" relates to the part of the fermentation medium comprising the calcium compound of the fermentation medium. Preferably, the calcium compound is provided in the form of a calcium salt, such as calcium chloride.

In an embodiment of the present invention the at least one precipitating trace metal compound; the one or more trace metal; or to both the precipitating trace metal compound and to the one or more trace metal may be dissolved by treating the at least one precipitating trace metal compound; the one or more trace metal; or to both the precipitating trace metal compound and to the one or more trace metal, with an acid or a chelating compound (e.g. a chelating buffer solution), providing an acidic dissolved composition or a chelated dissolved composition.

The acidic dissolved composition may preferably have a pH of 5.0 or below, such as a pH of 4.5 or below, e.g. a pH 4.0 or below, such as a pH of 3.5 or below, e.g. a pH 3.0 or below, such as a pH of 2.5 or below, e.g. a pH 2.0 or below, such as a pH of 1.5 or below, e.g. a pH 1.0 or below, such as a pH of 0.5 or below, e.g. a pH on the range of pH 0.5-5.0, such as in the range of pH 0.75-3, e.g. a pH on the range of pH 1.0-2.0, such as in the range of pH 1.25-1.5.

In a preferred embodiment of the present invention the acid used to provide the acidic dissolved composition may be an inorganic acid. In an embodiment of the present invention the acid used to provide the acidic dissolved composition, or the inorganic acid, may be selected from sulfuric acid or hydrochloric acid or a combination hereof.

In an embodiment of the present invention the acid used to provide the acidic dissolved composition may be an at least 80% concentrated acid, such as at least 85% concentrated acid, e.g. at least 90% concentrated acid, such as at least 92% concentrated acid, e.g. at least 95% concentrated acid, such as at least 96% concentrated acid, e.g. at least 97% concentrated acid, such as at least 98% concentrated acid, e.g. at least 99% concentrated acid.

In an embodiment of the present invention the main growth comprises one or more calcium compounds, in particular a calcium salt, such as calcium chloride.

As mentioned above, some of the advantageous of the present invention is that the new fermentation medium may result in a new process of methanotrophic organisms which may have a faster growth rate, may provide higher yield of cells, and the cells provided may have an improved viability, reducing the chance of precipitation of substrate composition and/or minimizing the risk for contamination.

In an embodiment of the present invention the at least one methanotrophic organism may be a methanotrophic bacterial cell selected from a *Methylococcus* strain.

In an even further embodiment of the present invention the *Methylococcus* strain may be *Methylococcus capsulatus*.

In even a further embodiment of the present invention, the at least one methanotrophic organism is selected from *M. capsulatus; Alcaligen acidovorans* (preferably NCIMB 13287); *Bacillus firmus* (preferably NCIMB 13280); and/or *Aneurobacillus danicus* (preferably NCIMB 13288). Preferably, the at least one methanotrophic organism comprises a combination of *M. capsulatus; Alcaligen acidovorans* (preferably NCIMB 13287); *Bacillus firmus* (preferably NCIMB 13280); and *Aneurobacillus danicus* (preferably NCIMB 13288).

In the context of the present invention, the term "trace metal solution" relates to a solution comprising the metals subset of trace elements; that is, metals normally present in small but measurable amounts in animal and plant cells and tissues and that are a necessary part of nutrition and physiology. Ingestion of, or exposure to, excessive quantities of trace metals can be toxic. However, insufficient plasma or tissue levels of certain trace metals can cause pathology, as is the case with iron. Trace metals may include iron, magnesium, lithium, zinc, copper, chromium, nickel, cobalt, vanadium, arsenic, molybdenum, manganese, selenium and others. Trace metals are metals needed by living organisms to function properly and are depleted through the expenditure of energy by various metabolic processes of living organisms.

In an embodiment of the present invention, the trace metal may be provided in form of a metal salt.

The trace metal may be provided in the form of a liquid composition, concentrate, or a solid composition. Preferably, the trace metal may be provided in the form of a liquid composition.

In an embodiment of the present invention, the trace metal solution may comprises a trace metal selected from the group consisting of one or more copper salts, such as copper sulphate; one or more zinc salts, such as zinc sulphate; one or more manganese salts, such as Manganese chloride; one or more molybdate salts, such as sodium molybdate; one or more cobalt salts, such as cobalt chloride; one or more nickel salts, such as nickel chloride; one or more iron salts, such as iron (II) sulphate or iron (II) chloride; or a combination hereof.

The trace metal solution may preferably be provided in a two-step procedure. In the present context, the term two-step procedure relates to the process of dividing the preparation of the trace metal solution in to two steps where some of the ingredients of the trace metal solution are mixed in on step providing a first trace metal solution and other (e.g. the remaining) ingredients are mixed in another step providing a second trace metal solution. The first trace metal solution and the second trace metal solution may subsequently be mixed either before the trace metal solution is mixed with the main growth solution in step (iv) of the method according to the present invention; or the first trace metal solution and the second trace metal solution may be added separately to the main growth solution in step (iv) of the method according to the present invention.

In the context of the present invention the term "precipitating trace metal" relates to the trace metals that tend to precipitate or cause precipitation during production of the trace metal solution and/or during production of the fermentation medium.

In an embodiment of the present invention the at least one precipitating trace metal compound may be a salt of the at least one precipitating trace metal compound. Preferably, the at least one precipitating trace metal compound may be an iron compound (an Fe-compound). Preferably, the precipitating trace metal may be iron ions.

In a further embodiment of the present invention the at least one precipitating trace metal compound or the Fe-compound may be selected from $Fe^{3+}$-compounds or $Fe^{2+}$-compounds, such as $FeCl_3.6H_2O$ or $FeSO4.7H_2O$.

The at least one precipitating trace metal compound may be dissolved by treating it with an acid or a chelating compound (e.g. a chelating buffer solution), providing an acidic dissolved composition or a chelated dissolved composition.

In an embodiment of the present invention the chelating compound may be selected from the group consisting of EDTA (Ethylenediaminetetraacetic acid); citric acid; porphyrin compounds; or chlorophyll compounds, preferably the chelating compound may be selected from EDTA or citric acid, even more preferably, the chelating compound may be EDTA.

Even chelating compounds may be used to dissolve the precipitating trace metal compound, the acidic dissolved compound may be preferred as the chelating compounds, in addition to dissolving the precipitating trace metal compound also add carbon source to the fermentation medium which may result in growth of unwanted microorganisms, which will affect or destroy the intended fermentation process.

In an embodiment of the present invention the one or more trace metal may be selected from the group consisting of a lithium compound, a zinc compound, a copper compound, a chromium compound, a nickel compound, a cobalt compound, a vanadium compound, a molybdenum, a manganese compound, and a lead compound.

Preferably, the one or more trace metal may comprise a combination of at least two of a zinc compound, a copper compound, a nickel compound, a cobalt compound, a molybdenum, a manganese compound, such as at least 3 of the compounds, e.g. at least 4 of the compounds, such as at least 5 of the compounds, e.g. all 6 of the compounds.

In an embodiment of the present invention the trace metal solution may be a transparent trace metal solution. Preferably, the trace metal solution may be a transparent trace metal solution without any precipitation. Even more preferably, the trace metal solution may be a transparent trace metal solution without any precipitation and having a slight greenish colour (when Cu, Cupper, is the dominating trace metal); a slight pinkish colour (when Co, Cobalt, is the dominating trace metal); slight whiteish (when Zn, Zinc, is the dominating trace metal); or slight yellowish (when Fe, Iron, is the dominating trace metal). In the context of the present invention, the term "the dominating trace metal" relates to the trace metal being present in the highest concentration in the trace metal solution.

The fermentation medium may comprise further ingredients improving the functionalities of the medium.

Hence, in an embodiment of the present invention the fermentation medium further comprises an anti-foaming solution and/or an anti-contaminating solution. Preferably, the mixing of the main growth solution (as provided in step (i) or (ii)) with the trace metal solution provided in step (iii) further includes mixing of an anti-foaming solution and/or an anti-contaminating solution providing the fermentation medium.

The fermentation medium may comprise a comprises a magnesium compound, such as a magnesium salt, preferably magnesium chloride ($MgCl_2$).

Hence, in an embodiment of the present invention the fermentation medium further comprises a magnesium compound, such as a magnesium salt, preferably magnesium chloride ($MgCl_2$). The magnesium compound may be part of the main growth solution provided in step (i) or in step (ii).

The fermentation medium may also comprise one or more buffer solutions. I, the method further comprises the step of adding a buffer solution. In an embodiment of the present invention, the buffer solution may be added to the main composition after the main composition has been mixed with the trace metal composition or the main composition has been mixed with the trace metal solution and the anti-foaming solution and/or an anti-contaminating solution, providing the fermentation medium.

In a further embodiment of the present invention the buffer solution is added to the fermentation medium before the fermentation medium is added to a fermentation reactor comprising at least one methanotrophic organism, or a combination of organisms comprising at least one methanotrophic organism.

In another embodiment of the present invention, the buffer solution is added directly to a fermentation reactor comprising at least one methanotrophic organism, or a combination of organisms comprising at least one methanotrophic organism.

The buffer solution may preferably comprise an acidic buffer solution, an alkaline buffer solution or a chelating buffer solution. Many different buffer solutions may be used during the fermentation process, however, the present inventor found that the buffer solution preferably comprises a phosphate buffer, such as sodium phosphate or potassium phosphate; a sulphate buffer, such as magnesium sulphate or sodium sulphate; and/or a chelating buffer solution, such as citric acid buffer or EDTA buffer; and/or a combination hereof.

In an embodiment of the present invention the fermentation medium may further comprise a nitrogen compound, such as a nitrate compound or an ammonium compound, preferably nitrate, such as sodium nitrate ($NaNO_3$).

Depending on the stage the fermentation medium is to be used the nitrogen source may be added to one or more different solutions. In an embodiment of the present invention the nitrogen compound is part of the main solution, the buffer solution or both, preferably the nitrogen compound is part of the main solution.

In an embodiment of the present invention the fermentation medium may be used in a fermentation process selected from a batch fermentation; a fed-batch fermentation; and/or a continuous fermentation.

In an embodiment of the present invention the fermentation medium is to be used in a batch fermentation and the nitrogen compound may be part of the main solution. Preferably, the nitrogen source during batch fermentation may nitrate, such as sodium nitrate ($NaNO_3$).

In a further embodiment of the present invention the fermentation medium may be a batch fermentation medium and the content of nitrogen compound is in the range of 0.5-12 g/l, such as in the range of 0.7-10 g/l, e.g. in the range of 1.0-5 g/l, such as in the range of 1.2-3 g/l, e.g. in the range of 1.5-2.0 g/l, such as about 1.7 g/l.

The fermentation medium may be used in a batch fermentation and the content of the one or more calcium compound in the batch fermentation medium, such as calcium chloride, may be 0.25 g/l or less, such as 0.2 g/l or less, e.g. 0.15 or less, such as 0.1 g/l or less, e.g. 0.05 or less, such as 0.01 g/l or less, e.g. 0.005 or less, such as in the range of 0.25-0.0001 g/l, e.g. in the range of 0.2-0.001 g/l, such as in the range of 0.15-0.01 g/l, e.g. in the range of 0.1-0.02 g/l, such as in the range of 0.08-0.03 g/l, e.g. in the range of 0.06-0.04 g/l.

In an embodiment of the present invention the fermentation medium is to be used in a fed-batch fermentation and the nitrogen compound may preferably be part of the main solution. Preferably, the nitrogen source during fed-batch fermentation may be a nitrate compound or an ammonium compound, even more preferably the nitrogen compound may be sodium nitrate ($NaNO_3$).

In a further embodiment of the present invention the fermentation medium may be a fed-batch fermentation medium and the content of nitrogen compound may be in the range of 15-35 g/l, such as in the range of 17-30 g/l, e.g. in the range of 19-25 g/l, such as in the range of 20-23 g/l, e.g. about 21.5 g/l.

The fermentation medium according to the present invention may be used in a fed-batch fermentation and the content of the one or more calcium compound, such as calcium chloride, in the fed-batch fermentation medium may be in the range of 0.05-10 g/l, such as in the range of 0.1-7.5 g/l, e.g. in the range of 1-5 g/l, such as in the range of 2.0-4.5 g/l, e.g. in the range of 3-4.2 g/l, such as in the range of 3.5-4 g/l.

In another embodiment of the present invention the fermentation medium is to be used in a continuous fermentation and the nitrogen compound may preferably be part of the main solution; the buffer solution; or both the main solution and the buffer solution. Preferably, the nitrogen source during fed-batch fermentation may be a nitrate compound or an ammonium compound, even more preferably the nitrogen compound may be an ammonium compound such as ammonium chloride and/or ammonium nitrate.

In a further embodiment of the present invention the fermentation medium may be a continuous fermentation medium and the content of nitrogen compound may be in the range of 15-35 g/l, such as in the range of 17-30 g/l, e.g. in the range of 19-25 g/l, such as in the range of 20-23 g/l, e.g. about 21.5 g/l.

The fermentation medium according to the present invention may be used in a continuous fermentation and the content of the one or more calcium compound, such as calcium chloride, in the continuous fermentation medium may be in the range of 0.05-10 g/l, such as in the range of 0.1-7.5 g/l, e.g. in the range of 1-5 g/l, such as in the range of 2.0-4.5 g/l, e.g. in the range of 3-4.2 g/l, such as in the range of 3.5-4 g/l.

The fermentation medium according to the present invention may preferably be an aqueous medium. In an embodiment of the present invention the fermentation medium may comprises tap water; demineralised water or a combination hereof. Preferably, the fermentation medium comprises demineralised water.

The water added to the various ingredient in order to provide the fermentation medium may influence on the composition as tap water may comprise various minerals that may be accounted for when preparing the fermentation medium. As the mineral content of tap water may fluctuate continuous analyses may be necessary to avoid under or over dosing the fermentation medium.

A preferred embodiment of the present invention relates to a fermentation medium comprising the following constituents: water; one or more calcium compounds, in particular calcium chloride; an acidic dissolved precipitating trace metal compound; one or more trace metals; and one or more buffer solutions, wherein none of the constituent's precipitates.

In an embodiment of the present invention the fermentation medium may be a batch fermentation medium. The batch fermentation medium may be used for the initial propagation of the organisms where all materials except the organisms, required may be decontaminated by autoclaving before loaded to the reactor together with the organisms and the process starts. The organism used may go through all the growth phases (lag phase, exponential phase and steady state phase. Under this operation mode, conditions may be continuously changed with time under unsteady-state system and requires a lot work and involvement.

In another embodiment of the present invention the fermentation medium may be a fed-batch fermentation medium. The fed-batch fermentation medium may be feed to the bioreactor during cultivation and in which the product/s remain in the bioreactor until the end of the run. The fed-batch fermentation medium may be used to provide high cell concentrations of the organism.

In a further embodiment of the present invention the fermentation medium may be a continuous fermentation medium. The continuous fermentation medium is added during the production mode of the fermentation process where feeding the microorganism with sterile continuous fermentation medium and at the same time, removing part of the fermentation liquid comprising the cells with spent medium from the system.

The inventor of the present invention surprisingly found that by preparing the fermentation medium as described herein none of the constituent's precipitates. In the present context, the term "none of the constituent's precipitates" relates to precipitation of one or more ingredients from the fermentation medium according to the present invention. Preferably, the term "none of the constituent's precipitates" relates to a solid content of the fermentation medium which is at most 5 g/l, such as at most 1 g/l, e.g. at most 0.5 g/l, such as an undetectable amount of solids (i.e. about 0 g/l).

Specific ingredients of a fermentation medium may be responsible for the precipitation. In the present invention, the calcium ions; the iron ions; and/or the phosphorous ions may be responsible for the precipitation of the fermentation medium.

In an embodiment of the present invention the fermentation medium comprises less than 0.05 g/l precipitated calcium, such as less than 0.03 g/l precipitated calcium, e.g. less than 0.01 g/l precipitated calcium, such as less than 0.005 g/l precipitated calcium, e.g. less than 0.001 g/l precipitated calcium, such as less than 0.0005 g/l precipitated calcium, e.g. less than 0.0001 g/l precipitated calcium, such as less than 0.00005 g/l precipitated calcium, e.g. less than 0.00001 g/l precipitated calcium.

In a further embodiment of the present invention the fermentation medium comprises less than 0.005 g/l precipitated iron, such as less than 0.003 g/l precipitated iron, e.g. less than 0.001 g/l precipitated iron, such as less than 0.0005 g/l precipitated iron, e.g. less than 0.0001 g/l precipitated iron, such as less than 0.00005 g/l precipitated iron, e.g. less than 0.00001 g/l precipitated iron.

In a further embodiment of the present invention the fermentation medium comprises less than 0.4 g/l precipitated phosphor, such as less than 0.3 g/l precipitated phosphor, e.g. less than 0.1 g/l precipitated phosphor, such as less than 0.05 g/l precipitated phosphor, e.g. less than 0.01 g/l precipitated phosphor, such as less than 0.001 g/l precipitated phosphor, e.g. less than 0.0001 g/l precipitated phosphor, such as less than 0.00001 g/l precipitated phosphor.

In yet an embodiment of the present invention, the trace metal solution and/or the fermentation medium according to the present invention may have a shelf life of at least 3 months without any precipitation may be observed, such as at least 6 months, e.g. at least 8 months, such as at least 10 months, e.g. at least 12 months, such as at least 15 months, e.g. at least 18 months, such as at least 24 months.

The present invention relates to a fermentation reactor comprising a reactor tank, one or more fermentation medium inlet, a fermentation liquid outlet for withdrawing fermentation liquid from the fermentation reactor and an ion sensor or analyser.

The fermentation reactor fermentation reactor may be supplied with a fermentation medium according to the present invention.

In an embodiment of the present invention the fermentation reactor may be a U-loop reactor comprising a loop-part with a circulation pump; and a degassing tank. The degassing tank may be a top-tank where the fermentation liquid may be subjected to degassing, removing exhaust gases from the fermentation liquid.

It may be important to control the content of different minerals and ions in the fermentation liquid during fermentation. Hence, the fermentation reactor is provided with an ion sensor or analyser for determining the content of one or more ion species in a fermentation liquid. Preferably the one or more ion species may be selected from phosphate, calcium, hydrogen, nitrate, ammonium and/or a combination hereof.

In an embodiment of the present invention the one or more fermentation medium inlet may be provided for introducing a fermentation medium according to the present invention into the fermentation reactor. The fermentation reactor according to the present invention may have at least 2 fermentation medium inlets, such as at least 3 fermentation inlets, e.g. at least 4 fermentation inlets.

In a further embodiment of the present invention a fermentation medium inlet may be provided for individual introduction of a main growth solution to the fermentation reactor.

In the present context, the term "individual introduction" relates to a separate inlet only providing the mentioned fermentation medium, or part of the fermentation medium, to the fermentation reactor. In this way, separate mixing tanks and separate mixing equipment does not need to be provided. Furthermore, is makes it possible to supply some ingredient and not others if the fermentation medium is only short in some ingredients and not in other.

In another embodiment of the present invention a fermentation medium inlet may be provided for individual introduction of a buffer solution to the fermentation reactor.

In an even further embodiment of the present invention a fermentation medium inlet may be provided for individual introduction of a trace metal solution to the fermentation reactor.

Examples of fermentation reactor design; use of sensors and analysers; and controlling of a fermentation reactor has been described in WO 2010/069313; and/or WO 2000/70014, which both are hereby incorporated by reference.

The present invention also relates to a fermentation process for production of biomass by cultivating at least one methanotrophic organism, or a combination of organisms comprising at least one methanotrophic organism, the method comprises the step of:
(a) supplying a fermentation medium according to the present invention to a fermentation reactor;
(b) adding at least one methanotrophic organism to the fermentation reactor;
(c) Allowing the at least one methanotrophic organism present in the fermentation medium to ferment, providing a fermentation liquid; and
(d) recovering the fermentation liquid from the fermentation reactor providing the biomass.

In an embodiment of the present invention the fermentation reactor may be a loop reactor as described herein or as described in WO 2010/069313; and/or WO 2000/70014, which both are hereby incorporated by reference.

The fermentation medium may comprise a main growth solution, a buffer solution, and/or trace metal solution, wherein the main growth solution, the buffer solution and/or the trace metal solution may be added separately or jointly to the fermentation reactor.

In an embodiment of the present invention the fermentation medium supplied in step (a) may include a start-up fermentation medium (a1) which is supplied during batch and/or fed-batch fermentation. The start-up fermentation medium (a1) may be a batch fermentation medium or a fed-batch fermentation medium.

The nitrogen source of the start-up fermentation medium may be a nitrate compound, such as sodium nitrate ($NaNO_3$). When the Start-up fermentation medium is a fed-batch fermentation medium the nitrate compound may be a nitrate compound or an ammonium compound; a nitrate compound, such as sodium nitrate ($NaNO_3$), may be preferred.

In another embodiment of the present invention the fermentation medium supplied in step (a) includes a production fermentation medium (a2) supplied during continuous fermentation, a continuous fermentation medium. The nitrogen source of the production fermentation medium may be an ammonium compound, such as ammonium chloride and/or ammonium nitrate.

In an embodiment of the present invention the fermentation process, during operation, starts as a batch fermentation process (using a batch fermentation medium), continuous to a fed-batch fermentation process (using a fed-batch fermentation medium) and wherein the nitrogen source in the batch fermentation medium and in the fed-batch fermentation medium may be a nitrate compound, such as sodium nitrate ($NaNO_3$). the fermentation process is a continuous fermentation where the production fermentation medium is added and in which production fermentation medium the nitrogen source is changes to an ammonium compound.

This, in an embodiment of the present invention the fermentation process involves a batch fermentation process and a fed-batch fermentation process using a fermentation medium having a nitrate compound as the nitrogen source, such as sodium nitrate, and a continuous fermentation process using ammonium as the nitrogen source.

In an embodiment of the present invention, part of the fed-batch fermentation may be supplied with fed-batch fermentation medium comprising a nitrate compound as the nitrogen source, such as sodium nitrate ($NaNO_3$) and another part of the fed-batch fermentation may be supplied with fed-batch fermentation medium comprising an ammonium compound as the nitrogen source, such as ammonium chloride and/or ammonium nitrate.

Preferably, the fermentation process is changed from batch fermentation or fed-batch fermentation to continuous fermentation when the biomass content is at least 15 g/l (e.g. $5-8\times10^6$ cells/ml), such at least 17.5 g/l, e.g. at least 20 g/l, such at least 25 g/l, e.g. at least 30 g/l, such at least 35 g/l, e.g. at least 40 g/l.

In an embodiment of the present invention, the fermentation medium is changed from batch fermentation medium or fed-batch fermentation medium to continuous fermentation medium when the biomass content is at least 15 g/l (e.g. $5-8\times10^6$ cells/ml), such at least 17.5 g/l, e.g. at least 20 g/l, such at least 25 g/l, e.g. at least 30 g/l, such at least 35 g/l, e.g. at least 40 g/l.

In order to ensure sufficient minerals and/or ions in the fermentation liquid one or more ion species of the fermentation liquid may be analysed during the fermentation process. Preferably, the one or more ion species is selected from phosphate, calcium, hydrogen, nitrate, and/or ammonium.

In an embodiment of the present invention a sensor or analyser may be used to analyse the one or more ion species, preferably, the sensor or analyser is an in-line sensor or an in-line analyser.

As mentioned previously the method according to the present invention results in an improved biomass production and an increased growth rate of the microorganism, such as a bacterial strain, e.g. a methanotrophic bacterial strain.

In a preferred embodiment of the present invention the method of the present invention provides a microbial growth rate during the fermentation process of at least 0.04 $h^{-1}$, e.g. at least 0.05 $h^{-1}$, such as at least 0.06 $h^{-1}$, e.g. at least 0.08 $h^{-1}$, such as at least 0.10 $h^{-1}$, e.g. at least 0.12 $h^{-1}$, such as at least 0.14 $h^{-1}$, e.g. at least 0.15 $h^{-1}$, such as at least 0.16 $h^{-1}$, e.g. at least 0.17 $h^{-1}$, such as at least 0.18 $h^{-1}$, e.g. at least 0.19 $h^{-1}$, such as at least 0.20 $h^{-1}$, e.g. at least 0.22 $h^{-1}$, such as at least 0.25 $h^{-1}$, e.g. at least 0.27 $h^{-1}$, such as at least 0.30 $h^{-1}$, e.g. at least 0.32 $h^{-1}$, such as at least 0.35 $h^{-1}$, e.g. at least 0.37 $h^{-1}$.

In another preferred embodiment of the present invention a biomass production of at least 2.5 g/l on a dry-matter basis may be provided, such as a biomass production of at least 2.6 g/l on a dry-matter basis may be provided, e.g. a biomass production of at least 2.7 g/l on a dry-matter basis may be provided, such as a biomass production of at least 2.8 g/l on a dry-matter basis may be provided, e.g. a biomass production of at least 2.9 g/l on a dry-matter basis may be provided, such as a biomass production of at least 3.0 g/l on a dry-matter basis may be provided, e.g. a biomass production of at least 3.5 g/l on a dry-matter basis may be provided, such as a biomass production of at least 4.0 g/l on a dry-matter basis is provided, e.g. a biomass production of at least 4.5 g/l on a dry-matter basis may be provided, such as a biomass production of at least 5.0 g/l on a dry-matter basis may be provided, e.g. a biomass production of at least 5.5 g/l on a dry-matter basis may be provided, such as a biomass production of at least 6.0 g/l on a dry-matter basis may be provided, e.g. a biomass production of at least 6.5 g/l on a dry-matter basis may be provided, such as a biomass production of at least 7.0 g/l on a dry-matter basis may be provided, e.g. a biomass production of at least 7.5 g/l on a dry-matter basis may be provided, such as a biomass production of at least 10.0 g/l on a dry-matter basis may be provided, e.g. a biomass production of at least 12.5 g/l on a dry-matter basis may be provided, such as a biomass production of at least 15.0 g/l on a dry-matter basis may be provided, e.g. a biomass production of at least 17.5 g/l on a dry-matter basis may be provided, such as a biomass production of at least 20.0 g/l on a dry-matter basis may be provided, e.g. a biomass production of at least 22.5 g/l on a dry-matter basis may be provided, such as a biomass production of at least 25.0 g/l on a dry-matter basis may be provided, e.g. a biomass production of at least 27.5 g/l on a dry-matter basis may be provided such as a biomass production of at least 30.0 g/l on a dry-matter basis may be provided.

The inventors of the present invention found, in addition to the improved biomass production and the increased growth rate that the high biomass production (or the maximum biomass production (in terms of g/l on a dry-matter basis) may be obtained significantly faster than traditional methods. Thus, in an embodiment of the present invention the high biomass production (or the maximum biomass production (in terms of g/l on a dry-matter basis) may be obtained in less than 5 days, such as in less than 4 days, e.g. in less than 3 days, such as in less than 2 days, e.g. in less than 24 hours, such as in less than 20 hours, e.g. in less than 16 hours, such as in less than 14 hours, e.g. in less than 12 hours, such as in less than 10 hours, e.g. in less than 8 hours.

In an embodiment of the present invention a biomass production of at least 3.5 g/l on a dry-matter basis is provided with in less than 24 hours, such as a biomass production of at least 4.0 g/l on a dry-matter basis is provided with in less than 20 hours, e.g. a biomass production of at least 4.5 g/l on a dry-matter basis is provided with in less than 14 hours, such as a biomass production of at least 5.0 g/l on a dry-matter basis is provided with in less than 10 hours, e.g. a biomass production of at least 5.5 g/l on a dry-matter basis is provided with in less than 8 hours.

As the fermentation medium according to the present invention the biomass obtained from the fermentation process using the fermentation medium may be considered being distinguishable from the biomass obtained from prior art fermentation processes.

As mentioned previously the fermentation medium according to the present invention has no or significantly no precipitation, in particular calcium precipitation; iron precipitation; and/or phosphate precipitation; as often is the case with a traditional fermentation medium. Hence, in an embodiment of the present invention the biomass product may have less than 10 mg/kg precipitated calcium, calcium phosphate, phosphate or iron, such as less than 5 mg/kg, e.g. less than 1 mg/kg, such as less than 0.5 mg/kg, e.g. less than 0.1 mg/kg, such as non-detectable amounts.

The protein product obtained by the fermentation process according to the present invention, using the unique fermentation medium according to the present invention may result in a unique protein product, wherein the protein product preferably has less than 10 mg/kg precipitated calcium, calcium phosphate, phosphate or iron, such as less than 5 mg/kg, e.g. less than 1 mg/kg, such as less than 0.5 mg/kg, e.g. less than 0.1 mg/kg, such as non-detectable amounts.

The biomass obtained by the present invention may be a single cell protein, being an edible unicellular microorganism. In an embodiment of the present invention the protein product according to the present invention, and/or the biomass according to the present invention may be used in a feed product or in a food product.

The protein product according to the present invention, and/or the biomass according to the present invention may be used in a fish feed or an animal feed, such as a pig feed, a cow feed, or a chicken feed.

It should be noted that embodiments and features described in the context of one of the aspects and/or one or more of the embodiments of the present invention also apply to the other aspects and/or other embodiments of the invention.

All patent and non-patent references cited in the present application, are hereby incorporated by reference in their entirety.

The invention will now be described in further details in the following non-limiting examples.

EXAMPLES

Example 1

The present example was performed to analyse precipitation of trace metals in the trace metal solution.

$FeCl_3$ was mixed with 10 ml 96% $H_2SO_4$ providing a concentration of 0.1 g/l $FeCl_3$ and resulted in an acidic dissolved composition comprising $FeSO4$ having a pH of about 2.

The acidic dissolved composition was then mixed with mixture of one or more trace metals comprising 0.04 g/l $CuCl_2$; 0.03 g/l $ZnCL_2$; <0.005 g/l $NaMoO_4$; <0.005 g/l $CoCl_2$; <0.005 g/l $MnCl_4$; and <0.005 g/l $NiCl_2$ providing the trace metal solution.

When precipitation is observed in the trace metal solution, an orange to brown colour is formed that is clear from visible inspection. The trace metal solution provided according to the present invention as illustrated in this Example showed a light yellowish, fully transparent trace metal solution, and without any precipitation at all.

Example 2

The present example was performed to analyse precipitation of trace metals in the trace metal solution.

A mixture of one or more trace metals comprising $CuCl_2$; $ZnCL_2$; $NaMoO_4$; $CoCl_2$; $MnCl_4$; and $NiCl_2$ was mixed with 10 ml 96% $H_2SO_4$ and resulted in an acidic dissolved composition comprising 0.04 g/l $CuCl_2$; 0.03 g/l $ZnCL_2$; <0.005 g/l $NaMoO_4$; <0.005 g/l $CoCl_2$; <0.005 g/l $MnCl_4$; and <0.005 g/l $NiCl_2$ and having a pH of about 2.

The acidic dissolved composition was then mixed with 0.1 g/l FeCl₃ providing the trace metal solution.

When precipitation is observed in the trace metal solution, an orange to brown colour is formed that is clear from visible inspection. The trace metal solution provided according to the present invention as illustrated in this Example showed a light yellowish, fully transparent trace metal solution, and without any precipitation at all.

Example 3

Shelf life test of the trace metal solutions provided in Examples 1 and 2.

The trace metal solutions provided in Examples 1 and 2 was left at room temperature without being subjected to light for 10 months. After the storage period no colour and no precipitation in the two trace metal solutions are observed.

Example 4

Standard NMS medium contains nitrate salt, sulphate salt and chloride with sodium, magnesium, calcium sources and a buffer, such as phosphate buffer, and a trace metal solution.

In the present experiment, two fermentation mediums were prepared, a standard NMS fermentation medium and a fermentation medium according to the present invention (as described in Example 1). The presence of too much calcium, as used in the standard NMS medium, exhibited to precipitate in the presence of phosphate buffer. Due to the precipitation of the standard NMS medium the growth of the bacteria slows down and growth is inhibited or lower to 0.05 $h^{-1}$ to 0.1 $h^{-1}$ from 0.17 $h^{-1}$. In standard NMS, trace metal always tends to form precipitation too.

In the fermentation medium according to the present invention (S-NMS) the fermentation medium was prepared as described in the present application and precipitation of calcium, phosphate and trace metals, in particular iron, was avoided, resulting in a growth rate of at least 0.16-0.2 $h^{-1}$.

The fermentation medium according to the present invention also showed to boost the start-up condition (the batch fermentation) and have shown to have stronger effect under fed-batch and continuous cultivation than conventional fermentation processes. In this fermentation medium the formulation of the trace metal solution is also done in a way where will precipitation of trace metals occur.

As ammonia is cheaper than nitrate ammonia may be the standard or preferred choice for any company as a substrate. But ammonia forms nitrite under any stressed conditions and bacteria cannot grow under certain nitrite levels. Nitrite forms bacteria inhibiting growth which is a condition that is not to be saved and which results in a so called "route of death".

Therefore, a novel fermentation growth medium as described in the present invention where nitrate may be used instead of ammonia under fed-batch phase after batch phase so that bacteria grow well without forming nitrite (and thus with a reduced risk of the "route of death"). Using the fermentation medium according the present invention is possible to achieve a biomass content in the range of 20-30 g/L. This level of biomass may be a highly interesting level to reach before start the continuous cultivation as the risk of facing the "route of death" is very small, almost not existing. The fermentation medium according to the present invention is capable of reaching the biomass amount of 20-30 g/L within 120 hours instead of failing fed-batch and start-up again and again using ammonia based medium. This media not only save the time but also save money for running different batches.

In conclusion, the results showed that maximum specific growth rate ($\mu^{max}$; 1/h) was significantly, and surprisingly, higher when cultivating a bacteria of the family Methylococcaceae, *Methylococcus capsulatus*, in a fermentation medium according to the present invention (S-NMS medium) rather than using a standard 2NMS.

The results showed a clear indication of higher growth rate when using the fermentation medium according to the present invention where precipitation in the 2NMS medium inhibits growth. The improved medium also showed to decrease the cultivation time during fed-batch fermentation from 120 hours to 24 hours and resulting in almost 4 times higher specific growth rate.

REFERENCES

WO 2010/069313
WO 2000/70014

The invention claimed is:

1. A method for providing a fermentation medium for the cultivation of at least one methanotrophic organism, or for the cultivation of a combination of organisms comprising at least one methanotrophic organism, the method comprises:
   (i) providing a main growth solution;
   (ii) optionally sterilizing the main growth solution provided in (i);
   (iii) providing a trace metal solution;
   (iv) mixing the main growth solution as provided in (i) or (ii) with the trace metal solution provided in (iii) and providing the fermentation medium for the cultivation of at least one methanotrophic organism, or for the cultivation of a combination of organisms comprising at least one methanotrophic organism,
wherein the trace metal solution is provided in a two-phase procedure and wherein the two-phase procedure involves:
   (v) providing at least one precipitating trace metal compound;
   (vi) providing one or more trace metals,
   (vii) mixing the at least one precipitating trace metal compound provided in (v) and the one or more trace metals provided in (vi), providing the trace metal solution;
wherein an acid is added to the precipitating trace metal compound, or to the one or more trace metals, or to both the precipitating trace metal compound and to the one or more trace metals separately, thereby providing an acidic dissolved composition, before the at least one precipitating trace metal compound provided in (v) and the one or more trace metals provided in (vi) are mixed, thereby providing the trace metal solution, wherein the acidic dissolved composition and/or the trace metal solution has a pH of pH 5.0 or below.

2. The method according to claim 1, wherein the at least one precipitating trace metal compound is a salt of the at least one precipitating trace metal compound.

3. The method according to claim 1, wherein the at least one precipitating trace metal compound is an iron compound.

4. The method according to claim 3, wherein the iron compound is selected from $Fe^{3+}$-compounds or $Fe^{2+}$-compounds.

5. The method according to claim 1, wherein the acid used for providing the acidic dissolved composition is selected from sulfuric acid or hydrochloric acid.

6. The method according to claim 1, wherein the acid is at least 80% concentrated acid.

7. The method according to claim 1, wherein the one or more trace metal is selected from the group consisting of a lithium compound, a zinc compound, a copper compound, a chromium compound, a nickel compound, a cobalt compound, a vanadium compound, a molybdenum, a manganese compound, and a lead compound.

8. The method according to claim 1, wherein the one or more trace metal comprises a combination of at least two of a zinc compound, a copper compound, a nickel compound, a cobalt compound, a molybdenum, a manganese compound.

9. The method according to claim 1, wherein the fermentation medium is for use in a batch fermentation that provides a batch fermentation medium that has one or more calcium compounds in the batch fermentation medium with a content of the one or more calcium compounds of 0.25 g/l or less.

10. The method according to claim 1, wherein the fermentation medium is for use in a fed-batch fermentation or a continuous fermentation that provides the fermentation medium containing one or more calcium compounds in a range of 0.05-10 g/l.

11. A fermentation medium obtainable by a method according to claim 1, wherein the fermentation medium comprises less than 0.05 g/l precipitated calcium; and/or wherein the fermentation medium comprises less than 0.005 g/l precipitated iron; and/or wherein the fermentation medium comprises less than 0.4 g/l precipitated phosphor.

12. A fermentation process for production of biomass by cultivating at least one methanotrophic organism, or a combination of organisms comprising at least one methanotrophic organism, the method comprises:
  (a) supplying a fermentation medium according to claim 11, to a fermentation reactor;
  (b) adding at least one methanotrophic organism into the fermentation reactor,
  (c) allowing the at least one methanotrophic organism present in the fermentation medium to ferment, providing a fermentation liquid; and
  (d) recovering the fermentation liquid from the fermentation reactor providing the biomass.

13. The fermentation process according to claim 12, wherein the fermentation process is a batch fermentation process or a fed-batch fermentation process and wherein the fermentation medium comprises a nitrogen source, preferably the nitrogen source is a nitrate compound, or wherein the fermentation process is a continuous fermentation where a production fermentation medium is added and in which production fermentation medium the nitrogen source is changed to an ammonium compound.

14. A method for preparing a fish feed or an animal feed, said method comprising the step of incorporating the biomass obtained by the fermentation process according to claim 12 into a fish feed or an animal feed.

15. A fermentation process for production of biomass by cultivating at least one methanotrophic organism, or a combination of organisms comprising at least one methanotrophic organism, the method comprises:
  (a) supplying a fermentation medium obtainable by a method according to claim 1, to a fermentation reactor;
  (b) adding at least one methanotrophic organism into the fermentation reactor,
  (c) allowing the at least one methanotrophic organism present in the fermentation medium to ferment, providing a fermentation liquid; and
  (d) recovering the fermentation liquid from the fermentation reactor providing the biomass.

16. The fermentation process according to claim 15, wherein the fermentation process is a batch fermentation process or a fed-batch fermentation process and wherein the fermentation medium comprises a nitrogen source, preferably the nitrogen source is a nitrate compound, or wherein the fermentation process is a continuous fermentation where a production fermentation medium is added and in which production fermentation medium the nitrogen source is changed to an ammonium compound.

17. A method for preparing a fish feed or an animal feed, said method comprising the step of incorporating the biomass obtained by the fermentation process according to claim 15 into a fish feed or an animal feed.

18. The method according to claim 1, wherein the acidic dissolved composition and/or the trace metal solution has a pH of pH 3.0 or below.

19. The method according to claim 1, wherein the acidic dissolved composition and/or the trace metal solution has a pH in the range of pH 0.75-3.0.

20. The method according to claim 1, wherein the fermentation medium is to be used in a batch fermentation and the content of the one or more calcium compounds in the batch fermentation medium is 0.05 g/l or less.

* * * * *